United States Patent [19]

Peck et al.

[11] 4,209,011
[45] Jun. 24, 1980

[54] DISPOSABLE SPLINT

[75] Inventors: Christopher M. Peck, Toronto; Eric R. Gozna, Scarborough, both of Canada

[73] Assignee: Camelia Manufacturing Co. Ltd., Toronto, Canada

[21] Appl. No.: 923,140

[22] Filed: Jul. 10, 1978

[30] Foreign Application Priority Data

Mar. 14, 1978 [CA] Canada .................................. 298887

[51] Int. Cl.² ............................................. A61F 5/04
[52] U.S. Cl. .................................... 128/87 R; 128/93
[58] Field of Search ............... 128/87 R, 83, 85, 84 R, 128/84 C, 93, 89 R

[56] References Cited
U.S. PATENT DOCUMENTS

| | | | |
|---|---|---|---|
| 2,409,195 | 10/1946 | Crawford | 128/87 R |
| 3,232,289 | 2/1966 | Zimmerman | 128/87 R |
| 3,496,934 | 2/1970 | Anderson | 128/93 X |
| 3,624,745 | 11/1971 | Bowers | 128/93 |
| 3,857,390 | 12/1974 | Harrison | 128/93 |
| 3,923,048 | 12/1975 | Schaar | 128/87 R |

*Primary Examiner*—John D. Yasko
*Attorney, Agent, or Firm*—Rogers, Bereskin & Parr

[57] ABSTRACT

A splint formed of a corrugated plastic material has a first elongated panel having a pair of laterally-spaced longitudinal fold lines that divide it into an inner base and first and second outer sidewalls. A second elongated panel is disposed rearwardly of the first panel and has a pair of laterally-spaced longitudinal fold lines that divide it into an inner base extension and first and second outer sidewall extensions. The first sidewall and the first sidewall extension are pivotable as a unit to a substantially upright position with respect to the base and the base extension, respectively, and the second sidewall and the second sidewall extension are also pivotable as a unit to a substantially upright position with respect to the base and the base extension, respectively. The first sidewall and the first sidewall extension are joined by a first removable portion and the second sidewall and second sidewall extension are joined by a second removable portion. Each removable portion extends from the inner edge of the sidewall outwardly to the outer edges of the sidewall and the sidewall extension and is bounded by a first pair of tear lines each of length greater than the lateral distance between the inner edge of the sidewall and the outer edge of the sidewall. Each tear line is defined by a series of spaced cuts in the corrugated plastic material. Upon removal of the removable portions, the rear panel is pivotable to a substantially upright position with respect to the inner base of the first panel, and the rear panel and the first panel have co-operating locking structure to lock the rear panel in the upright position. A similar splint with one end open and the other end foldable into a box is used to form a femoral splint having a windlass and a traction cord extending through the box end. A single panel with folding sides may be used to form a stretcher.

30 Claims, 27 Drawing Figures

DISPOSABLE SPLINT

This invention relates to a splint and stretcher formed of a corrugated plastic material.

The difficulties encountered at the scene of an accident in attending to a person having an injured limb are well known and many splints have been proposed for use in immobilizing the limb under such conditions. Examples of such prior art splints are shown in U.S. Pat. No. 2,409,195 of Oct. 15, 1946 to Crawford, U.S. Pat. No. 3,496,934 of Feb. 24, 1970 to Anderson; U.S. Pat. No. 3,624,745 of Nov. 30, 1971 to Bowers; U.S. Pat. No. 3,653,378 of Apr. 4, 1972 to Reuther; U.S. Pat. No. 3,850,167 of Nov. 26, 1974 to Seeley; and U.S. Pat. No. 3,896,799 of July 29, 1975 to Seeley.

The present invention in one aspect provides a novel splint formed of a corrugated plastic material which may be transported to a flat configuration to the scene of an accident, and there quickly and conveniently erected by folding, and by cutting if necessary, into a suitable configuration for use in immobilizing an injured upper arm, elbow, forearm, wrist, lower leg or ankle. The splint is lightweight, strong, waterproof, extremely inexpensive to manufacture, and can be penetrated by X-rays to eliminate unnecessary movement of the injured limb.

In one of its aspects the invention provides a splint or stretcher formed of a light, strong, relatively rigid corrugated plastic material. The splint or stretcher includes a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge. The plastic material includes a pair of spaced outer sheets forming outer surfaces of said material and a plurality of thin longitudinal ribs between the sheets, the ribs being oriented longitudinally in said panel member. The material is radiolucent so that it can be penetrated by X-rays.

In another of its aspects the invention provides, in the splint of the kind described above, a second elongated panel member disposed rearwardly of the first panel member. The second panel member has a third longitudinal scored fold line and a fourth longitudinal scored fold line spaced laterally from the third fold line, the third and fourth fold lines being substantially aligned with the first and second fold lines, respectively, and dividing the second panel member into an inner base extension, a first sidewall extension disposed outwardly of the third fold line and having an outer edge, and a second sidewall extension disposed outwardly of the fourth fold line and having an outer edge. The first sidewall and the first sidewall extension are pivotable along the first and third fold lines, respectively, to a substantially upright position with respect to the base and the base extension, respectively, and the second sidewall and the second sidewall extension are pivotable along the second and fourth fold lines, respectively to a substantially upright position with respect to the base and the base extension, respectively. The first sidewall and the first sidewall extension are joined by a first removable portion and the second sidewall and second sidewall extension are joined by a second removable portion. The first removable portion extends from the first fold line outwardly to the outer edges of the first sidewall and the first sidewall extension, and the second removable portion extends from the second fold line outwardly to the outer edges of the second sidewall and the second sidewall extension. The first removable portion is bounded by a pair of first tear lines and the second removable portion being bounded by a pair of second tear lines, each tear line being defined by a series of spaced cuts in the corrugated plastic material. Preferably the first tear lines are each of length greater than the lateral distance between the first fold line and the outer edge of the first sidewall, and the second tear lines are each of length greater than the lateral distance between the second fold line and the outer edge of the second sidewall.

In addition, in one aspect of the invention, the second panel member is pivotable, upon removal of the first and second removable portions, along a scored fold line extending laterally between the first and second longitudinal fold lines to a substantially upright position with respect to the inner base of the first panel member, and the first and second panel members have co-operating means to lock the second panel member in the upright position. Preferably the co-operating locking means includes a first male locking member defined in part by one of the first tear lines and a second male locking member defined in part by one of the second pair of tear lines.

Further aspects of the invention provide a femoral splint and a stretcher, as will be described.

Further aspects and advantages of the present invention will become apparent from the following description, considered in association with the accompanying drawings in which:

Figure 2:
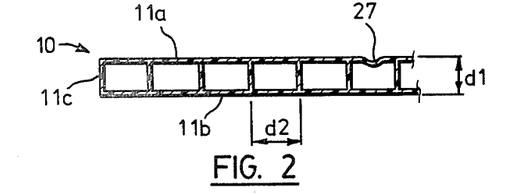
FIG. 2 is an enlarged sectional view along the line II—II of FIG. 1.

Reference is first made to FIG. 2. A disposable splint 10 constructed according to a preferred embodiment of the invention is formed from a corrugated plastic material sold under the trade mark COROPLAST by Coroplast Ltd., of Montreal, Quebec, Canada. The COROPLAST (trade mark) material has a very thin upper plastic sheet 11a which is joined to a very thin lower plastic sheet 11b by a plurality of very thin longitudinal plastic ribs 11c. Typically, the vertical distance d1 between the outer surfaces of the sheets 11a and 11b is of the order 4 mm., and the horizontal distance d2 between two adjacent ribs 11c is of the order 5 mm. A more complete description of the material is published by Coroplast Ltd. in its technical information brochures, and portions of that description are reproduced in Appendix A hereto.

Figure 1:
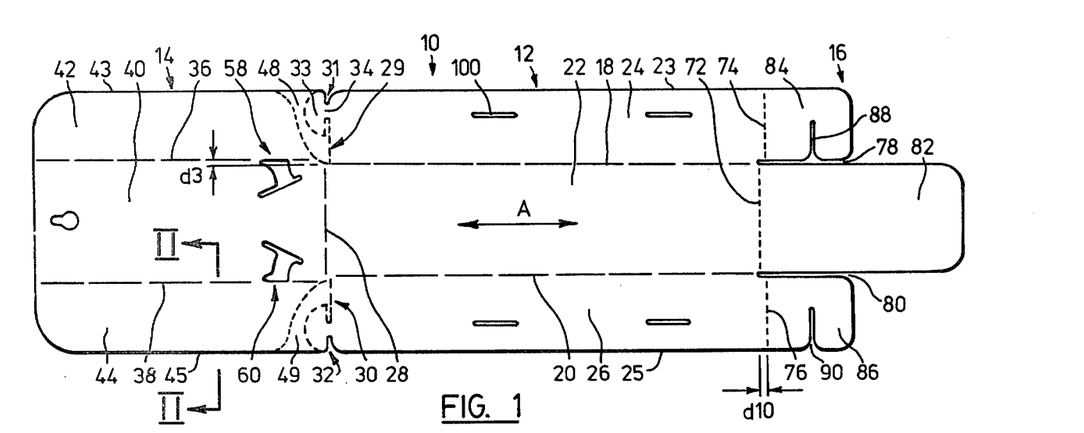
FIG. 1 is a top view of a disposable splint constructed according to a preferred embodiment of the invention.

Referring next to FIG. 1, the disposable splint 10 has a first elongated central panel member 12, a second elongated rear panel member 14, and a third elongated front panel member 16.

The central panel member 12 is provided with a first longitudinal scored fold line 18 and a second longitudinal scored fold line 20 spaced laterally from the scored fold line 18, the lines 18 and 20 dividing the panel member 12 into an inner base 22, a first sidewall 24 disposed outwardly of the first fold line 18 and having an outer edge 23, and a second sidewall 26 disposed outwardly of the second fold line 20 and having an outer edge 25. The scored fold lines 18 and 20 are formed by creasing the upper sheets 11a of the splint 10 to form a longitudinal notch 27 (FIG. 2) so as to permit convenient upward pivotal movement, but to prevent downward pivotal movement, of the sidewalls 24 and 26 about the lines 18 and 20, respectively.

The panel member 14 is separated from the panel member 12 by a scored fold line 28 extending laterally between the scored fold lines 18 and 20, by a first forward tear line 29 extending between the scored fold line 18 and the outer edge 23 of the first sidewall 24, and by a second forward tear line 30 extending between the scored fold line 20 and the outer edge 25 of the second sidewall 26. The tear lines 29 and 30 are shaped to define a pair of identical locking tabs 31 and 32 extending rearwardly from the sidewalls 24 and 26, respectively, the locking tab 31 having a broad head portion 33 and a narrow stem portion 34.

The scored fold line 28 is formed in the same manner as that in which the lines 18 and 20 are formed, and the manner in which the tear lines 29 and 30 are formed is discussed in detail hereinafter.

The panel member 14 is provided with a third longitudinal scored fold line 36 and a fourth longitudinal scored fold line 38 spaced laterally from the third fold line 36. The third and fourth scored fold lines 36 and 38 are each disposed outwardly of lines defined by the first and second fold lines 18 and 20, respectively, by a distance d3 (FIG. 1) approximately equal to the thickness d1 (FIG. 2) of the splint 10. The lines 36 and 38 divide the panel member 14 into an inner base extension 40 disposed rearwardly of the base 22, a first outer sidewall extension 42 disposed rearwardly of the sidewall 24 and having an outer edge 43, and a second outer sidewall extension 44 disposed rearwardly of the sidewall 26 and having an outer edge 45.

As indicated by arrow A in FIG. 1, the ribs 11c extend longitudinally (in the direction of arrow A) so that the splint will act as a board, with adequate stiffness, in the longitudinal direction.

Figure 3:
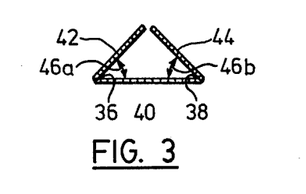
FIG. 3 is a rear end view of the disposable splint of FIG. 1 wherein the sidewalls and the sidewall extensions are pivoted to a second position.

Referring next primarily to FIG. 3, the sidewall 24 and the sidewall extension 42 are conveniently pivotable along axes defined by the first and third scored fold lines 18 and 36, respectively, from a first position where they are horizontally aligned with a plane defined by the base 22 and the base extension 40 to a second position where they form an acute angle 46a with respect to the plane. Typically, the angle 46a is approximately 45°.

Similarly, the sidewall 26 and the sidewall extension 44 are conveniently pivotable along axes defined by the second and fourth scored fold lines 20 and 38, respectively, from a similar first position to a similar second position where they form an acute angle 46b, which typically is also approximately 45°.

The sidewall extension 42 has a first removable forward portion 48 (FIG. 1) extending from the first scored fold line 18 outwardly to the outer edges 23 and 43 of the sidewall 24 and the sidewall extension 42, respectively. Similarly the sidewall extension 42 has a similar second removable forward portion 49 (FIG. 1) extending from the second scored fold line 20 outwardly to the outer edges 25 and 45 of the sidewall 26 and the sidewall extension 44, respectively.

When the portions 48 and 49 are removed, the sidewall extensions 42 and 44 are spaced from the sidewalls 24 and 26, respectively, so that the panel member 14 is then conveniently pivotable along an axis defined by the fold line 28 from a first position where it is horizontally aligned with a plane defined by the base 22 of the panel member 12 to a second position where it forms an acute angle 50 (FIG. 4) with respect to the plane. Typically, the angle 50 is approximately 45°.

Figure 5:
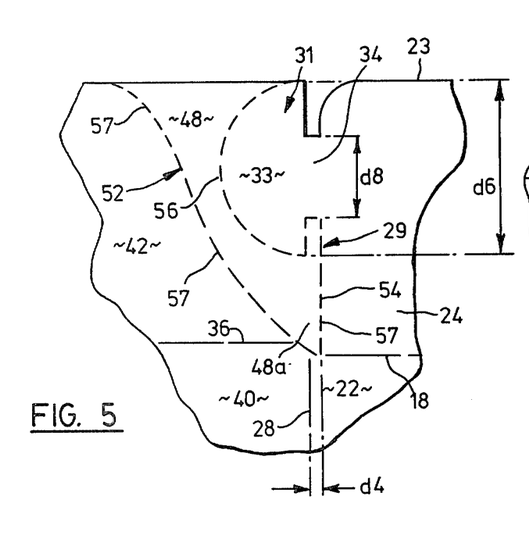
FIG. 5 is an enlarged top view of a first removable portion of the sidewall extension of the disposable splint of FIG. 1.

The first removable portion 48 is defined by a rear arcuate tear line 52 and by the forward tear line 29, as is best shown in FIG. 5. The tear line 29 has a first inner lateral section 54 and a second outer section 56 shaped to define in part the locking tab 31, the lateral section 54 being disposed forwardly of the scored fold line 28 by a distance d4 equal to the thickness d1 (FIG. 2) of the splint 10.

The tear lines 29 and 52 which define the first removable portion 48 are formed by first creasing the upper sheet 11a of the splint 10 to form a notch, and then making spaced cuts 57 in the upper sheet 11a, and as well in the lower sheet 11b, along the notch so that the first removable portion 48 can be conveniently removed by pressing on it with, for example, a finger.

It is desirable that the cuts 57 made in the outer portions of the tear lines 29 and 52 be of a smaller size than the cuts 57 made in the inner portions of the tear lines, so that the tear lines will be stronger near the outer edges than near the fold lines 18, 36. This is because when the sidewall extension 42 and the sidewall 24 are in their second pivoted positions (shown in FIG. 3), a restoring force in the sheets 11a and 11b of the plastic material forming the splint 10 tends to return the sidewall extension 42 and the sidewall 24 to their first horizontal positions. Consequently, to help to maintain rigidity and to avoid undesired separation of the sidewall extension 42 from the sidewall 24 when the support sections 24 and 42 are in their second pivoted positions, smaller-sized cuts (therefore leaving more uncut material) are made in the outer portions of the tear lines 29 and 52 where the restoring force is the greatest.

As well, when the base extension 40 is horizontally aligned with the base 22, and the sidewall extension 42 and the sidewall 24 are in their second positions, shown in FIG. 3, a load applied to, for example, the upper surface of the base extension 40 creates a bending moment which tends to cause the base extension 40 to pivot downwardly about the scored fold line 28. It is therefore also desirable that smaller-sized cuts 57 be made in the outer portions of the tear lines 29 and 52 as compared with the inner portions since the bending moment is greatest in the outer portions and the tear lines therefore should be strongest at the outer portions. This permits the splint 10 to act like a stiff board (for use in the configurations shown in FIGS. 12 and 14, as will be described) and helps to prevent the base extension from bending downwardly along the fold line 28.

Figure 7:
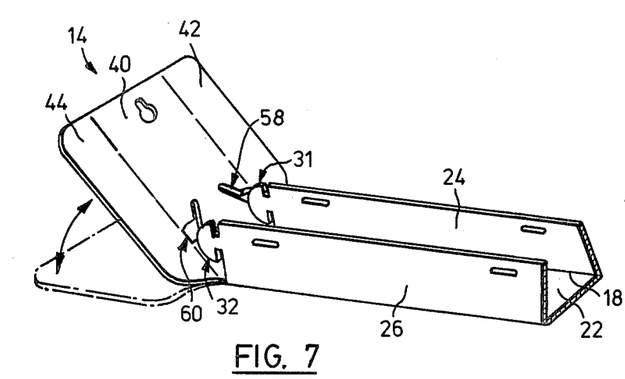
FIG. 7 is a perspective view of the disposable splint of FIG. 1 wherein the front panel member is removed and the rear panel member is being pivoted to an upright position.

Furthermore, the tear lines 29 and 52 each have a length longer than the lateral distance between the scored fold line 18 and the outer edge 23 of the sidewall 24. Therefore, the force created by the bending moment and applied perpendicularly to the uncut sections of the tear lines 29 and 52 so as to separate the sidewall extension 42 from the sidewall 24 is less than the force that would be applied to a laterally-extending tear line. In other words, since the tear lines 29 and 52 are longer than laterally-extending tear lines would be, and since they do not extend at right angles to the forces tending to separate the material along the tear lines, the possibility of undesirable separation of the plastic along the tear lines 29 and 52 is reduced. At the same time, the tear lines 29 and 52 can be made weak enough so that when the splint is to be folded as shown in FIG. 7, rather than to be used as a stiff board, the removable portions 48 and 49 can be removed by hand. Preferably for this purpose a small section 48a (FIG. 5), at the inner edge of each removable portion is fully cut, to allow the user to start the tear and to have a piece or tab to pull on. Once the user has detached and can pull on the tab 48a, he can more easy remove the remainder of the removable portion 48 by tearing along the tear lines 29, 52. In addition, preferably all of the ribs 11c (FIG. 2) are cut (i.e. the only uncut portions are between the ribs) to help the user to remove portions 48 and 49 by hand.

The base extension 40 of the panel member 14 is provided with a pair of identical tab slots 58 and 60 to receive the locking tabs 31 and 32, respectively so as to lock the panel member 14 and the sidewalls 24 and 26 in upright positions substantially perpendicular to the base 22 of the panel member 12.

Figure 6:
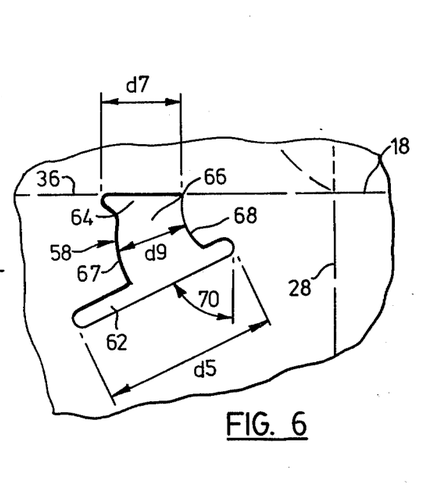
FIG. 6 is an enlarged top view of a tab slot of the inner base extension of the disposable splint of FIG. 1.

The tab slot 58 has a tab receiving portion 62, the height d5 (FIG. 6) of which is at least equal to the width d6 (FIG. 5) of the head portion 33 of the locking tab 31, a tab locking portion 64 disposed outwardly of the tab receiving portion 62, the height d7 (FIG. 6) of the locking portion 64 being equal to or very slightly greater than the width d8 (FIG. 5) of the stem portion 34 of the locking tab 31, and a tab passageway 66 connecting the receiving portion 62 with the locking portion 64, the passageway 66 having arcuately curved edge surfaces 67 and 68 and a height d9 (FIG. 6) at its narrowest slightly less than the width d8 (FIG. 5) of the stem portion 34.

The tab locking portion 64 is aligned with the scored fold line 36 whereas the tab receiving portion 62 is disposed at an angle 70 to the lateral scored fold line 28, the angle 70 being slightly greater than the angle 46a which the sidewall 24 makes in its second position with respect to the base 22.

To lock the panel member 14 and the sidewalls 24 and 26 in positions substantially perpendicular to the base 22 of the panel member 12 after the forward portions 48 and 49 of the sidewall extensions 42 and 44 have been removed, the sidewalls 24 and 26 of the panel member 12 are first pivoted to their second positions, as is clearly shown in FIG. 7. The panel member 14 is then pivoted to a substantially upright position and the locking tabs 31 and 32 fully inserted into the respective receiving portions of the tab slots 58 and 60. The stem portion 34 of the locking tab 31 is next pushed through the tab passageway 66 into the tab locking portion 64 to lock the second panel 14 and the sidewalls 24 and 26 in upright positions. Since the restoring force in the plastic material forming the splint 10 tends to return the sidewalls 24 and 26 to their first horizontal positions, little force is needed to push the locking tabs 31 and 32 through the passageways of their respective tab slots 58 and 60.

Considering next the front panel member 16 (FIG. 1), the panel member 16 is separated from the panel member 12 by an inner tear line 72 extending laterally between the scored fold lines 18 and 20, and by a pair of outer lateral tear lines 74 and 76 disposed forwardly of the tear line 72 by a distance d10 (FIG. 1) approximately equal to the thickness d1 (FIG. 2) of the splint 10. The tear lines 72, 74 and 76 are formed in a manner similar to that of the tear lines 29 and 52.

The front panel member 16 is provided with a first longitudinal slot 78 and a second longitudinal slot 80 spaced laterally from the slot 78, the slots 78 and 80 being substantially aligned with the scored fold lines 18 and 20 of the first panel member 12 and dividing the panel member 16 into an inner front wall section 82, a first front wall locking section 84 disposed outwardly of the slot 78, and a second front wall locking section 86 disposed outwardly of the slot 80. The locking section 84 has a first lateral slot 88 extending outwardly from the first longitudinal slot 78 which is aligned with a second lateral slot 90 extending inwardly from the outer edge of the locking section 86 towards the second longitudinal slot 80.

The inner front wall section 82 is pivotable along an axis defined by the tear line 72 from a first position where it is horizontally aligned with a plane defined by the base 22 of the panel member 12 to a second upright position where it is substantially perpendicular thereto.

Similarly, the outer front wall locking sections 84 and 86 are pivotable along axes defined by the tear lines 74 and 76, respectively, from first positions where they are horizontally aligned with planes defined by the sidewalls 24 and 26, respectively, to second upright positions where they are substantially perpendicular thereto.

Figure 8:
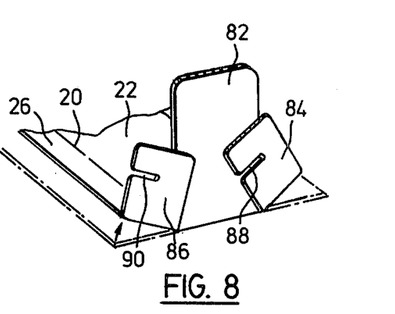
FIG. 8 is a perspective view of a front portion of the disposable splint of FIG. 1 wherein the front wall section and the front wall locking sections are in upright positions and the sidewalls are being pivoted to upright positions.
Figures 9, 10:
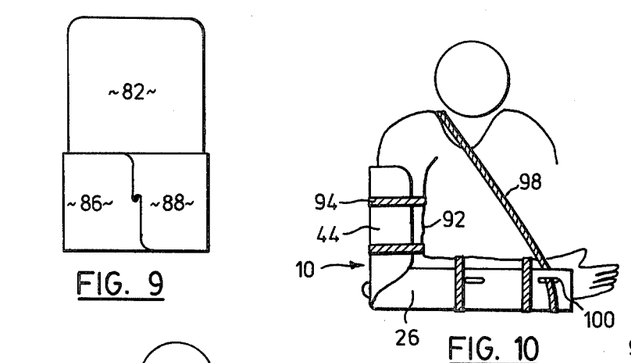
FIG. 9 is an end view of the disposable splint of FIG. 8 wherein the front wall section is locked in an upright position.
FIG. 10 is a view of the disposable splint of FIG. 1 being used in a first manner to immobilize an injured upper arm or elbow.

To lock the front wall section 82 of the panel member 16 in the upright position, it is first pivoted to the upright position (FIG. 8). Next, the front wall locking sections 84 and 86 are pivoted to their upright positions. The sidewalls 24 and 26 are then pivoted along the scored fold lines 18 and 20 to their upright positions to dispose the wall locking sections 84 and 86 forwardly of the wall section 82 whereupon the lateral slots 88 and 90 engage to lock together the wall locking sections 84 and 86 so as to prevent the wall section 82 from returning to its first horizontal position (FIG. 9). Since the restoring force in the plastic material forming the splint 10 tends to return the wall section 82 to its first position, the wall section 82 is constantly maintained in contact with the wall locking sections 84 and 86.

In use, it will be appreciated that the disposable splint 10 may be transported in a flat configuration to the scene of an accident, and there quickly and conveniently erected by folding, and by cutting if necessary, into a suitable configuration for use in immobilizing an injured upper arm, elbow, forearm, wrist, lower leg or ankle.

To immobilize an injured upper arm or elbow, the splint 10 can be used in any one of three ways, depending on the nature and extent of the injury. As shown in FIG. 10, it can be assembled in a configuration where the front panel member 16 is removed and the rear panel member 14 is locked in the upright position. The splint 10 is then snugly secured about the injured limb 92 by fastening material 94, such as, for example surgical tape or Velcro fastening strips, and, if desired supported by a sling 98 passed through slots 100 in the sidewalls 24 and 26 of the central panel member 12.

Figure 11:
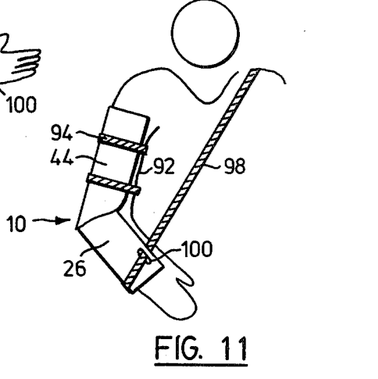
FIG. 11 is a view of the disposable splint of FIG. 1 being used in a second manner to immobilize an injured upper arm or elbow.

Alternatively, as shown in FIG. 11, the rear panel member 16 need not be locked in the upright position but can be in a position intermediate between the horizontal and upright positions. It is maintained in the desired position by snugly securing the splint 10 about the injured limb 92 by fastening material 94.

Figure 12:
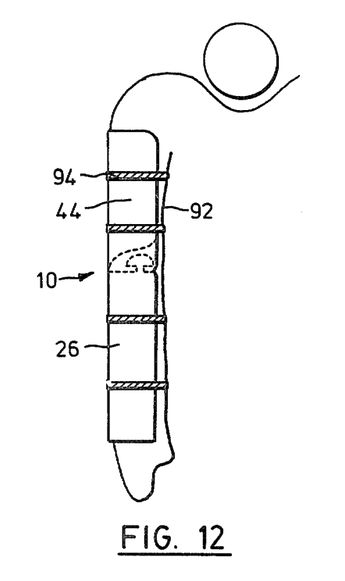
FIG. 12 is a view of the disposable splint of FIG. 1 being used in a third manner to immobilize an injured upper arm or elbow.

As well, as shown in FIG. 12, the injured upper arm or elbow can be immobilized in an extended position. After the front panel member 16 is removed, the sidewalls 24 and 26 and the sidewall extensions 42 and 44 are pivoted to upright positions and the splint 10 snugly secured about the injured limb 92 by fastening material 94.

Figure 13:
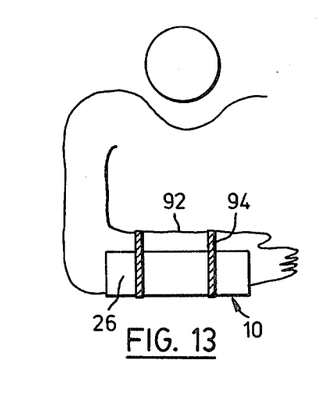
FIG. 13 is a view of the disposable splint of FIG. 1 being used to immobilize an injured wrist or forearm.

To immobilize an injured wrist or forearm, the splint 10 is assembled in a configuration shown in FIG. 13 wherein the front panel member 16 and the rear panel member 14 are typically removed. The sidewalls 24 and 26 are disposed in upright positions and the splint 10 snugly secured about the limb by fastening material 94. The rear panel member 14 need not be removed if it is desired as well to immobilize the hand. If required, the splint 10 can be cut in the field to shorten the length of the central panel member 12.

Figure 14:
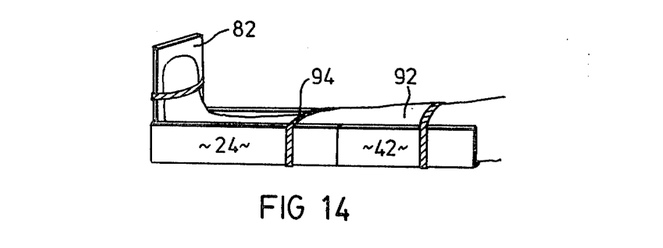
FIG. 14 is a view of the disposable splint of FIG. 1 being used to immobilize an injured lower leg.

To immobilize an injured lower leg, the front wall section 82 of the front panel member 16 is locked in the upright position as shown in FIG. 14, and the splint 10 secured snugly about the injured limb by bandaging material 92, the foot of the leg being disposed against the front wall section 82.

Figure 15:
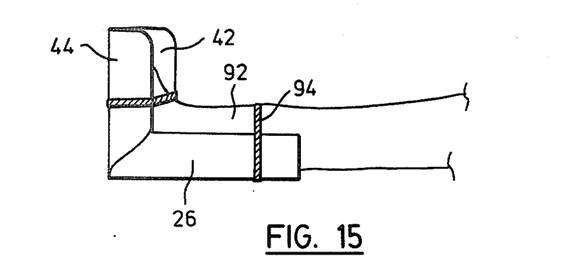
FIG. 15 is a view of the disposable splint of FIG. 1 being used to immobilize an injured ankle.

To immobilize an injured ankle, the front panel member 16 is removed and the rear panel member 14 locked in the upright position as shown in FIG. 15, and the splint 10 secured snugly about the injured limb by bandaging material 92, the foot being disposed against the base extension 40 of the rear panel member 14.

It will be appreciated that with the splint 10 it is not necessary to move an injured limb to a substantial extent. The splint 10 can be conveniently disposed about the injured limb (for example, by sliding the splint 10 under the lib), then erected by folding to the desired configuration and subsequently snugly secured about the limb. If required, padding material may be inserted between the splint 10 and the injured limb.

As well, it may be adapted in the field by cutting and folding so as to be used with any size of injured limb, and instructions as to its use in various emergencies can be conveniently printed on it.

The splint 10 is waterproof and can be penetrated by X-rays. Consequently, there is little need to change from time to time under adverse weather conditions the splint immobilizing an injured limb, and it need not be removed immediately upon arrival at a hospital.

Various modifications may be made to the preferred embodiment of the invention. For example, a button or a clip arrangement can be used in place of the locking tabs and tab slots to lock the front wall locking section 84 to the front wall locking section 86 and, as well, the sidewall extensions 42 and 44 to the sidewalls 24 and 26, respectively.

As indicated, the splint 10 is waterproof and can be penetrated by X-rays. Consequently, there is little need to change from time to time under adverse weather conditions the splint immobilizing an injured limb, and it need not be removed immediately upon arrival at a hospital, since the patient can be promptly X-rayed without removing the splint. Although the plastic material is not fully transparent to X-rays (some shadows do appear), it is found that these shadows do not interfere with the interpretation of the X-rays, i.e. there is no difficulty in distinguishing between bone (and bone fractures) and shadows produced by the plastic. Since the plastic, though not fully transparent to X-rays, is much more so than bone, it may be termed radiolucent.

Various modifications may be made to the splint, described. For example the male locking tabs 31, 32 may extend from the sidewall extensions 42, 44 instead of from the sidewalls 24, 26, and the tab slots 58, 60 will then be located in the base 22 instead of the base extension 40.

Figure 16:
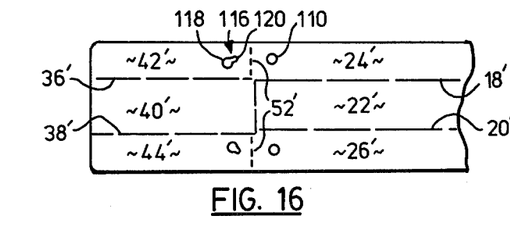
FIG. 16 is a plan view of another splint according to the invention.
Figure 17:
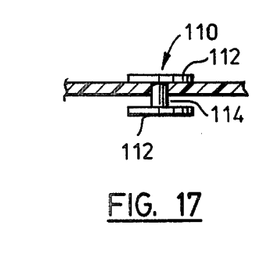
FIG. 17 is an edge view showing a locking bottom of the FIG. 16 splint.

Alternatively, a separate button or clip arrangement can be used in place of the locking tabs and tab slots to lock the front wall locking section 84 to the front wall locking section 86 and, as well, the sidewall extensions 42 and 44 to the sidewalls 24 and 26, respectively. This is shown in FIGS. 16 and 17 where primed reference numerals indicate parts corresponding to those of the previous Figures. In FIGS. 16 and 17, a plastic button 110 is provided, having spaced disc-like ends 112 joined by a narrow shaft 114. Such buttons are presently commercially available in two halves which when pushed together lock together. One button is secured to each sidewall 24', 26', and each sidewall extension 42', 44' includes an appropriately located tearshaped slot 116. Each slot 116 has an enlarged entrance 118 to receive the button end 112 and a narrower retaining end 120 through which will pass the button shaft 114 but not the button end 112.

Figure 4:
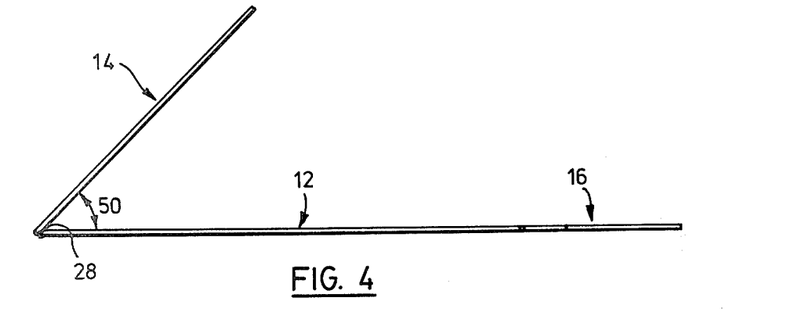
FIG. 4 is a side view of the disposable splint of FIG. 1 wherein the rear panel member is pivoted to a second position.

In use, when the splint is to be folded in the manner of FIG. 4, tear lines 52' are torn or severed, the splint 101 is folded in the manner of FIG. 4, and the buttons 110 are inserted into slots 116 to lock the splint in folded condition.

Figure 18:
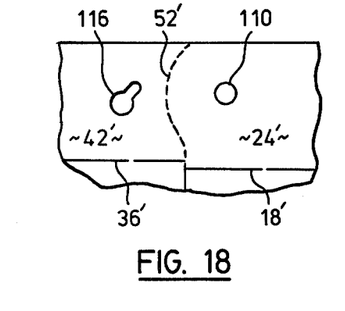
FIG. 18 is a plan view showing a modification of the FIG. 16 splint.

It will be noted that no removable portions are shown in FIGS. 16 and 17, but only tear lines 52'. The tear lines are preferably again stronger at the outside edges of the splint than adjacent the fold lines 18', 20', since the stresses are greatest at the edges of the splint. Although the tear lines 52' are shown as transverse to the fold lines 18', 20', preferably again they are made longer than the transverse distance between fold lines 18', 20' and the edges of the splint. This is shown at 52' in FIG. 18 and again gives added strength to the tear lines. It should be added that although the embodiment of FIGS. 16 and 17 is useful, the previously shown embodiment is much preferred, since it is cheaper to make, easier to separate along the tear lines (since it is easier to remove a punch-out or removable portion than tear along a single tear line), and easier to lock in folded condition.

Figure 19:
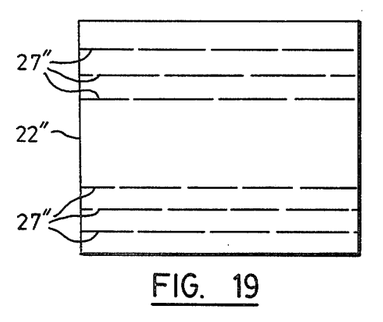
FIG. 19 is a plan view showing a further modified splint.

In some applications of the splint the front panel member 16 may be eliminated, and even the rear panel member 14 may also be eliminated in some applications. In addition, if it is desired to have a roll-top for the splint, more than one fold line such as score line 27 may be provided, as indicated by fold lines 27" in the single panel 22" shown in FIG. 19. If it is desired to have the splint reversible, the fold lines 27" can be scored in both surfaces (front and back) of the splint. Alternatively the scored fold lines can be constituted by lines of perforations through both sides of the plastic material forming the splint. Such a line will form a fold line, but a creased line such as that shown at 27 in FIG. 1 is preferred since it weakens the material less than a line of perforations.

Reference is next made to FIGS. 20 to 24, which show a splint 210 similar to that of FIG. 1 but which may be used as a femoral splint, for immobilizing or applying traction to an injured upper leg. The splint 210 is of course of the same corrugated plastic material, e.g. that sold under the trade mark COROPLAST, as the other splints described, with the ribs 11c extending longitudinally of the splint, in the direction of arrow A.

Figure 20:
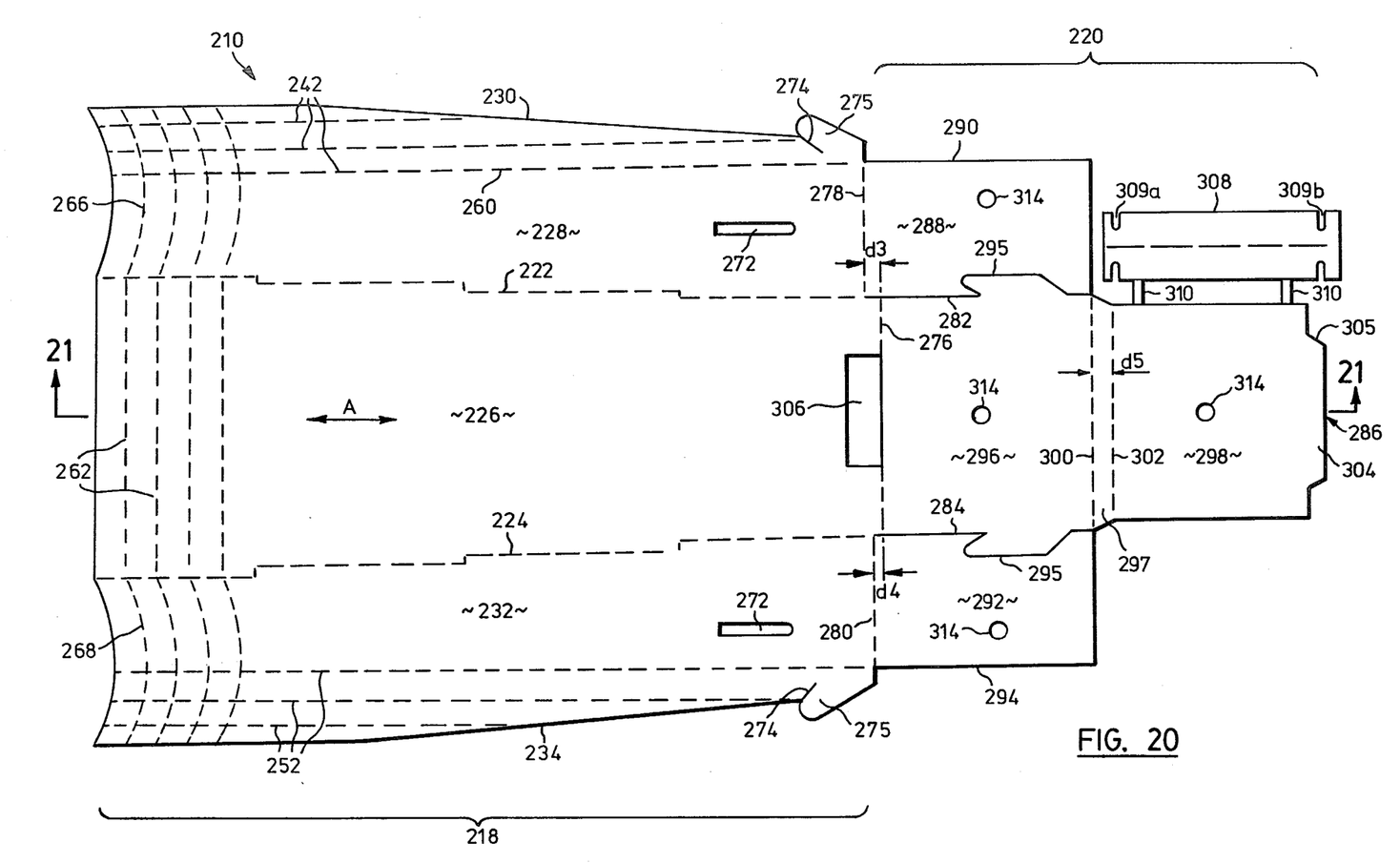
FIG. 20 is a top view of a disposable femoral splint constructed according to the invention.

The splint 210 has an elongated rear panel 218 and a shorter front panel 220. The rear panel 218 has a first substantially longitudinal scored fold line 222 and a second substantially longitudinal scored fold line 224 spaced laterally from the scored fold line 222. The fold lines 222 and 224 diverge slightly in a rearward direction and divide the rear panel 218 into an inner base 226, a first sidewall 228 disposed outwardly of the first fold line 222 and having an outer edge 230, and a second sidewall 232 disposed outwardly of the second fold line 224 and having an outer edge 234. The outer edges 230 and 234 diverge in a rearward direction.

The sidewalls 228, 232 have a number of parallel longitudinal scored fold lines 242, 252 respectively. These lines facilitate bending the outer portions of the sidewalls over the top of the patient's leg, as will be explained. The scored fold lines 242, 252 are formed by first creasing the upper sheet 11a of the splint 210 to form a notch, and then making a series of spaced cuts 260 (FIG. 20) in the upper sheet 11a along the notch, and as well in the lower sheet 11b, so that the splint 210 can be conveniently folded along any one of the fold lines. The spaced cuts (not shown) in the lower sheet 11b are disposed slightly inwardly of the spaced cuts in the upper sheet 11a to permit convenient bending of the splint 210 about the particular fold line. The perforations or cuts in the fold lines reduce the resilience of the fold and hence reduce the tendancy of the folded material to "spring back".

The rear portion of the rear panel 218 has a series of perforated cut lines 262, each of which extends generally transversely between the outer edges 230 and 234 of the sidewalls 228 and 232, respectively. The outer portions 266 and 268 of each cut line 262 are concavely curved to fit the patient's groin area.

Each cut line 262 is formed by first creasing the upper sheet 11a of the splint 210 to form a notch (not shown), and then making a series of spaced cuts 270 in the upper sheet along the notch, and as well in the lower sheet 11b, so that the splint 210 can be readily cut along the cut line 262. The lines 262 are typically spaced about 2 inches apart in the direction of arrow A.

The forward portions of sidewalls 228, 232 each have a longitudinally extending windlass shot 272. The slot 272 is located approximately half way between the scored fold lines 222 and 224 and the innermost longitudinal fold lines 242 and 252, respectively.

In addition, the forward portions of the sidewalls 228 and 232 have an inwardly and forwardly extending slit 274, which defines a jam cleat 275, used for a purpose to be explained.

The front panel 220 is separated from the rear panel 218 by an inner scored fold line 276 extending laterally between the scored fold lines 222 and 224, and by a pair of outer lateral scored fold lines 278 and 280 disposed rearwardly of the inner fold line 276 by distances d3 and d4 respectively. Distance d3 is approximately equal to three or four times the thickness d1 (FIG. 2) of the splint 10, while distance d4 is about half of distance d3.

The panel 220 includes a first longitudinal fully cut line 282 and a second longitudinal fully cut line 284 spaced from the first line 282. The fully cut lines 282 and 284 divide the front panel 20 into a front wall locking section 286, a first outer front wall flap 288 disposed outwardly of the first cut line 282 and having an outer edge 290, and a second outer front wall flap 292 disposed outwardly of the second cut line 284 and having an outer edge 294. The cut lines 284 also defined gripping ears 295 projecting outwardly from locking section 286, for a purpose to be explained.

The first and second front wall flaps 288 and 292 are pivotable along the outer lateral fold lines 278 and 280, respectively, from positions where they are aligned with the first and second outer sidewalls 228 and 232, respectively, to positions where they are substantially perpendicular thereto.

The front wall locking section 286 is pivotable along the lateral inner fold line 276 from a position where it is horizontally aligned with the inner base 226 of the rear panel 218 to a position where it is substantially perpendicular thereto. The locking section 286 consists of a first inner portion 296, a second thin central portion 297 and a third outer portion 298. The portion 297 is separated from the first and third portions 296, 298 by laterally extending scored fold lines 300 and 302 respectively. The thickness d5 of the central portion 297 is approximately equal to three to four times the thickness d1 (FIG. 2) of the splint 210.

The third outer portion 293 of the front wall locking section 286 has a forwardly extending tab 304. The tab 304 has sloping sides 305 and is slightly wider at its base than a tab receiving slot 306 disposed in the inner base 226 of the rear panel member 218 adjacent to the fold line 276.

An elongated windlass 308, the use of which is hereinafter described, is attached to a side edge of the third outer portion 298 by pieces of material 310. The windlass 308 can be easily broken away from the pieces of material 310 and folded along fold line 312 for use in the manner hereinafter described. The windlass 308 has slots 309a, 309b adjacent its ends, the slots extending in a direction at right angles to the axis of the windlass.

In use, the disposable femoral splint 210 may be transported in a flat configuration to the scene of an accident, and there quickly and conveniently erected by folding, and by cutting if necessary, into a suitable configuration for use in immobilizing and applying traction to an injured upper leg.

Before the splint 210 is applied to immobilize and to apply traction to an injured upper leg, the length of the uninjured leg is measured, and the splint 210 is then cut along a cut line 262 to the proper length for use. The splint 210 is cut so that the distance from the fold line 276 to the particular tear line 262 is about one foot greater than the length of the uninjured leg. The windlass 308 is also removed from the splint 210 at this time.

Next, a foam groin pad (not shown) is applied to the appropriate outer portion 266 or 268 of the cut line 262, depending on which leg is injured.

The splint 210 is next assembled by pivotting its sidewalls 228, 232 to a generally perpendicular position with respect to the inner base 276. The front wall flaps 288, 292 are then pivotted along the fold lines 278, 280 respectively to their perpendicular positions, with wall section 292 lying outside wall section 288. Next the front wall locking section 286 is pivoted to an upright position along the fold line 276. The outer portion 298 of the locking section 286 is then pivoted behind the wall flaps 288 and 292, the tab 304 being inserted into the tab receiving slot 306 to lock the sections 286, 290 and 292 in their perpendicular positions.

After the splint has been erected, a standard traction harness 316 (FIG. 21) having a traction cord 318 with portions 318a and 318b is next attached to the injured leg 320, and steady longitudinal traction is applied to the leg 320 by pulling on the cord portions 318a and 318a. The splint 210 is then positioned about injured leg 320 so that the groin pad (not shown) fits snugly in the groin area of the injured person. If necessary, additional groin padding may of course be used. The sidewalls 228 and 232 are then folded about the injured leg and secured to it with a suitable fastening material 322, such as a Velcro (trade mark) strip or surgical tape.

The traction cord 318 is next passed through the aligned apertures 314 in the sections 286, 288 and 292. Each portion 318a, 318b of the cord 318 is then pulled upwardly over the top of the folded front wall (FIG. 22) and is then pulled rearwardly and inserted into one of the slits 274. The cord sections are then pulled downwardly and forwardly around the jam cleats, along the outer sidewalls of the splint, are passed under the gripping ears 295, and are then firmly tied forwardly of the portions 296 of the front wall locking section 286, at a knot 321.

Figure 21:
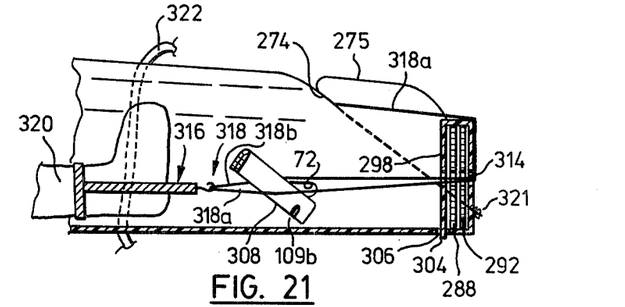
FIG. 21 is a sectional view taken along lines 21—21 of the splint of FIG. 20 after the splint has been erected and also shows a patient's foot in the splint.
Figure 22:
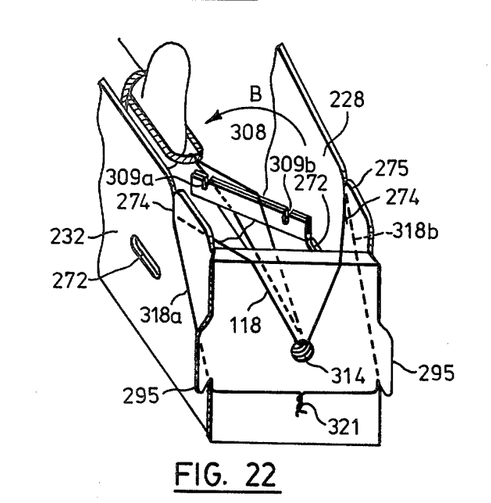
FIG. 22 is a perspective view of the erected splint of FIG. 21 showing a windlass stick being used to tighten a traction harness therein.
Figure 23:
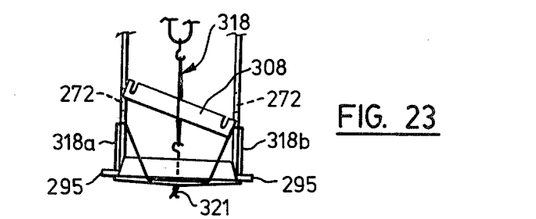
FIG. 23 is a top view of the erected splint of FIG. 21, showing the windlass stick about to be inserted into its slots.
Figure 24:
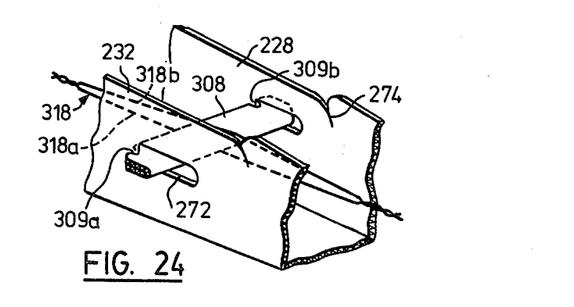
FIG. 24 is a perspective view of a portion of the FIG. 21 splint, showing the windlass stick being engaged in slots in the splint.

Next, the windlass 308 is folded along the fold line 312 and is inserted between the cord portions 319a and 319b rearwardly of the sections 286, 288 and 292 (FIG. 21). The windlass 308 is then rotated as indicated by arrow B (FIG. 22) to twist the cord 318 to apply traction to the leg. When the desired amount of traction has been applied, the windlass 308 is placed in a horizontal plane (FIG. 23) and its ends are inserted into the windlass stick receiving slots 272. The windlass 308 is then slide rearwardly until the slots 309a and 309b in the windlass 308 engage the sidewalls which define the rear ends of the slots 272. This prevents the windlass 308 from becoming dislodged and hence prevents the cord 318 from untwisting.

With the femoral splint 210 described, it is not necessary to move an injured leg to a substantial extent. The femoral splint 210 can be erected, disposed about the injured leg (for example, by sliding the splint 210 under the leg), and then snugly secured about the leg. If required, padding material may be inserted between the splint 10 and the injured leg.

If desired, other suitably rigid box arrangements may be used for the front wall of the femoral splint. For example the box structure provided by the rear panel 14 of the FIG. 1 splint may be used. In all cases a hole will be provided in the front wall of the splint for the traction cord. In addition a jam cleat will preferably be provided.

Figure 25:
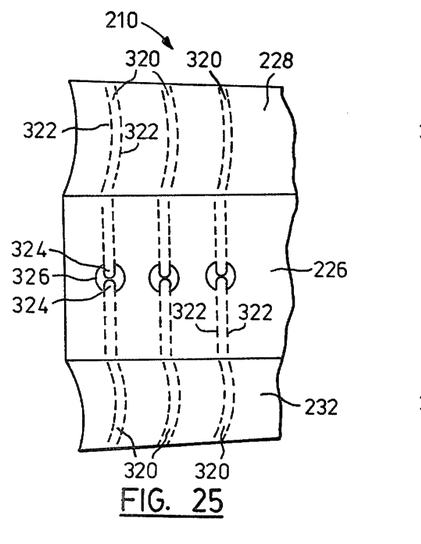
FIG. 25 is a top view showing tearable end portions for the splint of FIG. 21.

As discussed, the splint of FIGS. 20 to 24 must be cut to length, to suit the patient in question. The length may vary considerably, depending on whether the patient is a child or an adult, and the persons using the splint may not always have scissors available. Therefore, as shown in FIG. 25, tear strips 320 may be provided for the splint 210. As shown in FIG. 25 each tear strip consists of a pair of parallel closely spaced tear lines 322 extending from the outer edge of the sidewalls 228, 232 inwardly to the centre of the base panel 226. The tear lines 322 terminate in a tab 324 located in a central aperature 326. As before, the cuts which form the tear lines 322 are of a smaller size at the outer portions of the tear lines than at the inner portions, so that the tear lines will be stronger near the outer edges than near the central aperture 326. The cuts of tear lines 322 are in fact the same as the cuts 57 of tear lines 29 and 52 (FIG. 5), and the tabs 324 function in exactly the same way as removable portions 48a (FIG. 5) so that they may be gripped to begin the tearing process. The longitudinal spacing between the tear strips 320 is typically about 2 inches, so that the length of the femoral splint may be adjusted in two inch increments, without the need for scissors. The tear lines 322 may be curved as shown to confirm as closely as possible to the expected shape of the average patient's groin area.

Figure 26:
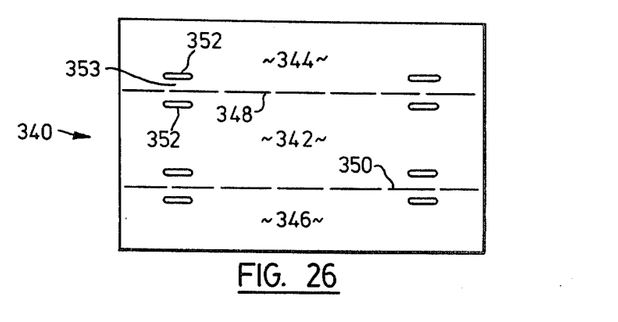
FIG. 26 is a plan view of a stretcher according to the invention.
Figure 27:
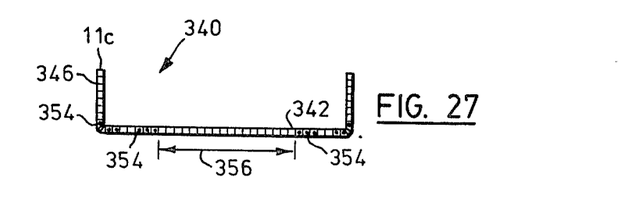
FIG. 27 is a sectional view of the stretcher of FIG. 27, shown in erected condition.

Finally, reference is made to FIGS. 26 to 28, which show a stretcher 340 according to the invention. The stretcher 340 consists of an elongated inner base 342 and a pair of outer sidewalls 344, 346, integrally joined to the base 342 at scored fold lines 348, 350. Hand holes 352 are punched in the sidewalls 344, 346 and in the base 342, leaving handles 353 between pairs of adjacent hand holes so that the handle 353 may be gripped by a user. As before, the ribs 11c (FIG. 2) of the corrugated plastic material used for the stretcher extend longitudinally, to provide the required stiffness in the longitudinal direction.

In use, the sidewalls 344, 346 are folded upwardly into a vertical plane. A patient is then placed on the stretcher, and moved as required.

If desired, high tensile strength steel wires 354 (FIG. 27) may be inserted into the spaces between the ribs 11c (except for those spaces intersected by holes 352). The ends of the wires may be hooked (not shown) to secure them within the spaces. If wires are used, they will normally be arranged to leave a longitudinal area 356 along the patient's axial skeleton free of wires, so that X-rays may be taken through the stretcher. Normally area 356 will be about one foot wide, since this is all that is required in order to X-ray a patient's spine. The presence of the wires extending through the handles 353 helps the strengthen the handles. However, if sufficiently thick corrugated plastic material is used, the wires will not normally be necessary. The COROPLAST (trade mark) corrugated plastic material of 5mm thickness has been tested for stretcher purposes and has been found to possess excellent strength.

APPENDIX A

COROPLAST (trade mark) is a continuously extruded corrugated plastic sheet formed from a blend of co-polymer resins (polypropylene-polyethylene) developed and patented by Tokan Kogyo Co. Ltd. of Tokyo, Japan. The product is available in various gauges (e.g. from 2mm. to 5mm.) and varying weights or densities (from 400 gms/$M^2$ to 1000 gms/$M^2$). It is waterproof, has high impact resistance, can withstand temperatures from 106° C. to −35° C. (220° F. to −30° F.), has a high strength to weight ratio, and is resistant to a wide range of acids, alkalis, chemicals, greases and oils. It can be electrostatically treated to accept screen printing, it can be stitched, glued, ultrasonic-welded, heat sealed, die-cut, scored, creased and folded.

Various properties for three representative gauges and densities are as follows:

1. MECHANICAL PROPERTIES

|  | Gauge | 2.0mm | 4.0mm | 4.0mm |
|---|---|---|---|---|
|  | gms/sq.m. Weight | 400 | 700 | 800 |
|  | lbs/sq.ft. | .082 | .143 | .164 |
| a) Impact Strength* | | | | |
| 23° C. (73.4° F.) | kg/cm | 9.5 | 15.8 | 18.0 |
|  | lbs/in | 53.2 | 88.5 | 101.0 |
| 0° C. (32° F.) | kg/cm | 8.9 | 16.2 | 18.5 |
|  | lbs/in | 50.0 | 90.7 | 103.5 |
| −20° C. (−4° F.) | lbs/in | 37.8 | 62.7 | 71.5 |
| b) Tensile Strength** | | | | |
| Load | kg | 16.9 | 28.1 | 32.0 |
|  | lbs | 37.4 | 62.0 | 70.6 |
| Yield Point | kg/$cm^2$ | 34.4 | 46.5 | 53.0 |
|  | lbs/$in^2$ | 461.2 | 661.5 | 750.8 |
| Point of Failure | kg/$cm^2$ | 241.0 | 240.2 | 276.0 |
|  | lbs/$in^2$ | 3443.1 | 3417.0 | 3887.0 |
| Elongation | % | 166.8 | 166.3 | 166.3 |

*A.S.T.M. D-781-59T
**A.S.T.M. D-828-60

2. COMPRESSIONS STRENGTH

|  | Gauge | 2.0mm | 4.0mm | 4.0mm |
|---|---|---|---|---|
|  | Weight gm/lbs | 400/.082 | 700/.143 | 800/.164 |
| a) Flat Crush | | | | |
| Load | kg | 13.3 | 16.3 | 18.5 |
|  | lb | 28.9 | 36.0 | 42.0 |
| Compression | kg/$cm^2$ | 0.54 | 0.65 | 0.74 |
|  | lbs/$in^2$ | 7.5 | 9.2 | 10.5 |
| Strain | % | 1.04 | 1.04 | 1.09 |
| b) Machine Direction Compression | | | | |
| Load | kg | 32.5 | 39.8 | 45.2 |
|  | lb | 72.05 | 87.75 | 99.95 |
| Compression | kg/$cm^2$ | 16.2 | 19.7 | 22.4 |
|  | lbs/$in^2$ | 232.1 | 280.25 | 321.0 |
| Strain | % | 2.15 | 2.37 | 2.5 |
| c) Transverse Direction Compression | | | | |
| Load | kg | 2.5 | 2.9 | 3.3 |
|  | lb | 5.25 | 6.4 | 7.3 |
| Compression | kg/$cm^2$ | 1.23 | 1.5 | 1.72 |
|  | lb/$in^2$ | 17.5 | 21.3 | 24.4 |
| Strain | % | 1.9 | 1.7 | 1.8 |

*A.S.T.M. D-781-59T
**A.S.T.M. D-828-60

THE ABOVE TESTS WERE PERFORMED IN THE LABORATORY OF TOKAN KOGYO CO., LTD. OF TOKYO, JAPAN USING THE FOLLOWING:

(a) IMPACT TEST—DUPONT IMPACT TESTER (b) TENSILE TEST—INSTRON MATERIAL TESTER (c) COMPRESSION TEST—TENSILON MATERIAL TESTER

3. FLEXING STRENGTH

In the Shell Chemical Laboratory in London, England, several pieces of Coroplast were subjected to Flexing Tests and the results were as follows:

(a) Sample One—Test was terminated after 270,000 flexes due to machine breakdown.

(b) Sample Two—Test was terminated after 4,000 flexes due to machine breakdown.

(c) Sample Three—Test was suspended after machine showed 1,000,000 flexes.

RESULTS

None of the samples showed any visible evidence of fatigue.

What I claim as my invention is:

1. A splint formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said splint further including a second elongated panel member disposed rearwardly of the first panel member, the second panel member having a third longitudinal scored fold line and a fourth longitudinal scored fold line spaced laterally from the third fold line, the third and fourth fold lines being substantially aligned with the first and second fold lines, respectively, and dividing the second panel member into an inner base extension, a first sidewall extension disposed outwardly of the third fold line and having an outer edge, and a second sidewall extension disposed outwardly of the fourth fold line and having an outer edge, the first sidewall and the first sidewall extension being pivotable along the first and third fold lines, respectively, to a substantially upright position pivotable along the second and fourth fold lines, respectively, to a substantially upright position with respect to the base and the base extension, respectively, the first sidewall and the first sidewall extension being joined by a first tear line and the second sidewall and second sidewall extension being joined by a second tear line, the first tear line extending from the first fold line outwardly to the outer edge of the first sidewall, the second tear line extending from the second fold line outwardly to the outer edge of the second sidewall, the first tear line being of length greater than the lateral distance between the first fold line and the outer edge of the first sidewall, the second tear line being of length greater than the lateral distance between the second fold line and the outer edge of the second sidewall, each tear line being defined by a series of spaced cuts in the corrugated plastic material.

2. A splint formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said splint further including a second elongated panel member disposed rearwardly of the first panel member, the second panel member having a third longitudinal scored fold line and a fourth longitudinal scored fold line spaced laterally from the third fold line, the third and fourth fold lines being substantially aligned with the first and second fold lines, respectively, and dividing the second panel member into an inner base extension, a first sidewall extension disposed outwardly of the third fold line and having an outer edge, and a second sidewall extension disposed outwardly of the fourth fold line and having an outer edge, the first sidewall and the first sidewall extension being pivotable along the first and third fold lines, respectively, to a substantially upright position pivotable along the second and fourth fold lines, respectively, to a substantially upright position with respect to the base and the base extension, respectively, the first sidewall and the first sidewall extension being joined by a first tear line and the second sidewall and second sidewall extension being joined by a second tear line, the first tear line extending from the first fold line outwardly to the outer edge of the first sidewall, the second tear line extending from the second fold line outwardly to the outer edge of the second sidewall, the first tear line being of length greater than the lateral distance between the first fold line and the outer edge of the first sidewall, the second tear line being of length greater than the lateral distance between the second fold line and the outer edge of the second sidewall, each tear line being defined by a series of spaced cuts in the corrugated plastic material.

3. A splint as defined in claim 2 wherein said first tear lines are each of length greater than the lateral distance between the first fold line and the outer edge of the first sidewall, and said second tear lines are each of length greater than the lateral distance between the second fold line and the outer edge of the second sidewall.

4. A splint as defined in claim 2 wherein the second panel member is pivotable, upon removal of the first and second removable portion, along a scored fold line extending laterally between the first and second longitudinal fold lines to a substantially upright position with respect to the inner base of the first panel member, the first and second panel members having co-operating means to lock the second panel member in the upright position.

5. A splint as defined in claim 4 wherein the co-operating locking means includes a first male locking member defined in part by one of the first tear lines and a second male locking member defined in part by one of the second tear lines.

6. A splint as defined in claim 3 wherein the second panel member is pivotable, upon removal of the first and second removable portions, along a scored fold line extending laterally between the first and second longitudinal fold lines to a substantially upright position with respect to the inner base of the first panel member, the first and second panel members having co-operating means to lock the second panel member in the upright position.

7. A splint as defined in claim 6 wherein the co-operating locking means includes a first male locking member defined in part by one of the first tear lines and a second male locking member defined in part by one of the second tear lines.

8. A splint as defined in claim 7 wherein the male locking members are a pair of locking tabs, one extending rearwardly from each sidewall and each having a broad head portion and a narrow stem portion, and the co-operating locking means includes a pair of tab slots disposed in the base extension and each having a tab receiving portion, the height of the receiving portion being at least the width of the head portion, a tab locking portion, the height of the locking portion being at least the width of the stem portion, and a tab passageway connecting the receiving portion with the locking portion, the height of the passageway being slightly less than the width of the stem portion.

9. A splint as defined in claim 7 wherein the male locking members are a pair of locking tabs, one extending forwardly from each sidewall extension and each having a broad head portion and a narrow stem portion, and the co-operating locking means includes a pair of tab slots disposed in the base and each having a tab receiving portion, the height of the receiving portion being at least the width of the head portion, a tab locking portion, the height of the locking portion being at least the width of the stem portion, and a tab passageway connecting the receiving portion with the locking portion, the height of the passageway being slightly less than the width of the stem portion.

10. A splint as defined in claim 7, further comprising: a third elongated panel member disposed forwardly of the first elongated panel member, the third panel member having a first longitudinal slot and a second longitudinal slot spaced laterally from the first longitudinal slot, the first and second slots dividing the third panel member into an inner front wall section, a first outer front wall locking section disposed outwardly of the first slot and having an outer edge, and a second outer front wall locking section disposed outwardly of the second slot and having an outer edge, the front wall section being pivotable along a lateral inner fold line from a position where it is horizontally aligned with the inner base of the second panel member to a position where is is substantially perpendicular thereto, the first and second front wall locking sections being pivotable along a pair of outer lateral fold lines from positions where they are aligned with the first and second outer sidewalls, respectively, to positions where they are substantially perpendicular thereto, the front wall locking sections having co-operating locking means to lock the front wall section in the perpendicular position.

11. A splint as defined in claim 10 wherein the outer lateral fold lines are disposed forwardly of the inner lateral fold line by an amount equal to the thickness of the corrugated plastic material.

12. A splint as defined in claim 1 wherein the first and second longitudinal slots are substantially aligned with the first and second fold lines, respectively, of the first panel member.

13. A splint as defined in claim 10 or claim 13 wherein the first front wall locking section has a first lateral slot extending outwardly from the first longitudinal slot and the second front wall locking section has a second lateral slot extending inwardly from the outer edge of the second locking section towards the second longitudinal slot, the first and second lateral slots being substantially aligned, such that when the first and second front wall locking sections are in their substantially perpendicular positions and the first and second sidewalls are pivoted along the first and second scored fold lines, respectively, of the first panel member to upright positions, the first and second lateral slots engage to lock together the first and second front wall locking sections.

14. A splint as defined in claim 1, 2 or 3 wherein the third and fourth longitudinal scored fold lines are each disposed outwardly of the first and second scored fold lines, respectively, by an amount equal to the thickness of the corrugated plastic material.

15. A splint as defined in claim 1, 2 or 3 wherein said cuts in each tear line are made through all of said ribs crossed by such tear lines.

16. A splint as defined in claim 1, 2 or 3 wherein said cuts in each tear line are made through all of said ribs crossed by such tear line, and wherein at least some of the cuts in said tear lines are longer adjacent said fold lines than adjacent said outer edges so that said tear lines are weaker adjacent said fold lines than adjacent said outer edges.

17. A splint as defined in claim 4, 5 or 6 wherein said cuts in each tear line are made through all of said ribs crossed by such tear lines.

18. A splint as defined in claim 4, 5 or 6 wherein said cuts in each tear line are made through all of said ribs crossed by such tear line, and wherein at least some of the cuts in said tear lines are longer adjacent said fold lines than adjacent said outer edges so that said tear lines are weaker adjacent said fold lines than adjacent said outer edges.

19. A splint as defined in claim 7, 8 and 10 wherein said cuts in each tear line are made through all of said ribs crossed by such tear lines.

20. A splint as defined in claim 7, 8 or 10 wherein said cuts in each tear line are made through all of said ribs crossed by such tear line, and wherein at least some of the cuts in said tear lines are longer adjacent said fold lines than adjacent said outer edges so that said tear lines are weaker adjacent said fold lines than adjacent said outer edges.

21. A splint formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said splint further including second panel member means connected to said first panel member and foldable with said first and second sidewalls to form a front wall box end for said splint, said front wall including an aperture thin for a traction cord, so that a traction cord may be passed through said aperture and tightened against said front wall to apply traction to a limb within said splint.

22. A splint as defined in claim 21 wherein said first and second sidewalls each have a windlass stick receiving slot therein, and including an elongated windlass stick for twisting the cord to apply a desired traction to the injured limb, the windlass stick being dimensioned for its ends to fit within said slots thereby to maintain the desired traction by preventing the cord from untwisting.

23. A splint formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said splint further including a second elongated panel member disposed forwardly of the first panel member, the second panel member having a front wall locking section pivotally connected to said inner base along an inner lateral fold line and pivotal along said inner lateral fold line from a position where it is horizontally aligned with the inner base of the first panel member to a position where it is substantially perpendicular thereto, a first outer front wall flap disposed outwardly of said front wall locking section on one side thereof and pivotally connected to said first sidewall along a first lateral fold line, and a second outer front wall flap disposed outwardly of said front wall locking section on the other side thereof and pivotally connected to said second sidewall along a second lateral fold line, said first and second front wall flaps being pivotable along said first and second lateral fold lines from positions where they are aligned with the first and second outer sidewalls, respectively, to positions where they are substantially perpendicular thereto, the front wall locking section having an inner portion, thin central portion and an outer portion, the outer portion being pivotable behind the front wall flaps when the said sections are substantially perpendicular to the sidewalls, the sidewalls being folded perpendicular to said inner base, the outer portion having a male locking means which engages with a female locking means in the first panel member to lock the said sections in substantially upright position, said front wall locking section and said front wall flaps together constituting a front wall for said splint and said inner and outer portions of said front wall locking section and said front wall flaps having holes which are aligned when said splint is erected for a cord which is used to apply traction to an injured upper leg immobilized in said splint.

24. A splint according to claim 23 wherein the first and second sidewalls each have a longitudinally extending windlass stick receiving slot, and an elongated windlass stick for twisting said cord to apply a desired traction to the injured leg, the windlass stick being dimensioned for its ends to fit within the windlass stick receiving slots thereby to maintain the desired traction by preventing the cord from untwisting.

25. A splint according to claim 21, 23 or 24 wherein said first and second sidewalls are each of greater height than said front wall when said splint is assembled and each of said sidewall has a downwardly and forwardly extending slit in the upper edge thereof adjacent said front wall, and said front wall includes a pair of locking ears one at each side thereof, so that said cord may be passed through the aperture in said front wall, and then portions of said cord may be drawn through said slits and under said locking ears and tied together over said front wall.

26. A disposable femoral splint according to claim 21, 23 or 24 wherein said windlass stick is also formed from said plastic material and comprises first and second identical longitudinally extending layers, said layers lying one against the other and being integrally joined at a fold line therebetween.

27. A disposable splint as defined in claim 24 wherein the second panel member is pivotable, upon removal of the first and second removable portion, along a scored fold line extending laterally between the first and second longitudinal fold lines to a substantially upright position with respect to the inner base of the first panel member, the first and second panel members having co-operating means to lock the second panel member in the upright position, said windlass stick being removably integrally connected to one of said panel members.

28. A splint formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said splint further including a laterally extending removable end portion defined by a tab and a pair of closely spaced tear lines extending from said tab to the outer edge of said sidewall, said tear lines defining a tear strip, each tear line being defined by a series of spaced cuts in the corrugated plastic material, at least some of the cuts in said tear lines being longer adjacent said tab than adjacent said outer edge so that said tear lines are weaker adjacent said tab than adjacent said outer edge.

29. A splint as defined in claim 28 and including an aperture in said base and a pair of said tear strips, each tear strip extending from an outer edge of said sidewall inwardly towards the other tear strip and terminating at said aperture, the tab of each tear stip being located in said aperture.

30. A stretcher formed of a light, strong, relatively rigid corrugated plastic material, comprising: a first elongated panel member having a first longitudinal scored fold line and a second longitudinal scored fold line spaced laterally from the first fold line, the first and second fold lines dividing the first panel member into an inner base, a first sidewall disposed outwardly of the first fold line and having an outer edge, and a second sidewall disposed outwardly of the second fold line and having an outer edge, said plastic material including a pair of spaced outer sheets forming outer surfaces of said material and a plurality of thin longitudinal ribs between said sheets, said ribs being oriented longitudinally in said panel member, said material being radiolucent, said stretcher further and including a plurality of stiffening wires extending longitudinally through the spaces between said ribs, said stretcher having a central area at least approximately one foot wide free of said wires, so that X-rays may be taken through said central area.

* * * * *